United States Patent

Klieger et al.

[11] 4,132,731
[45] Jan. 2, 1979

[54] NOVEL IODIZED ISOPHTHALAMIC ACID COMPOUNDS

[75] Inventors: Erich Klieger; Ulrich Speck, both of Berlin, Fed. Rep. of Germany

[73] Assignee: Schering Aktiengesellschaft, Berlin and Bergkamen, Fed. Rep. of Germany

[21] Appl. No.: 806,383

[22] Filed: Jun. 14, 1977

[30] Foreign Application Priority Data

Jun. 25, 1976 [DE] Fed. Rep. of Germany ....... 2629228

[51] Int. Cl.$^2$ ..................... C07C 63/12; A61K 29/02
[52] U.S. Cl. ......................................... 424/5; 562/451
[58] Field of Search ............................ 200/519; 424/5

[56] References Cited

U.S. PATENT DOCUMENTS

| | | | |
|---|---|---|---|
| 3,622,616 | 11/1971 | Guerbet et al. | 260/519 |
| 3,660,464 | 5/1972 | Bernstein et al. | 260/519 |
| 3,886,203 | 5/1975 | Felder et al. | 260/519 |
| 3,912,776 | 10/1975 | Pfeiffer et al. | 260/519 |
| 3,914,294 | 10/1975 | Bernstein et al. | 260/519 |
| 3,939,204 | 2/1976 | Buttermann | 260/519 |
| 3,953,497 | 4/1976 | Wiegert | 260/519 |
| 4,001,298 | 1/1977 | Gries et al. | 260/519 |
| 4,014,986 | 3/1977 | Tilly et al. | 260/519 |
| 4,032,567 | 6/1977 | Klieger et al. | 260/519 |

*Primary Examiner*—James O. Thomas, Jr.
*Assistant Examiner*—James H. Reamer
*Attorney, Agent, or Firm*—Millen & White

[57] ABSTRACT

Iodized isophthalamic acid compounds of the formula

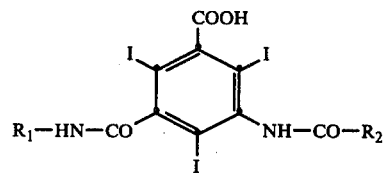

wherein
$R_1$ is straight-chain or branched lower hydroxyalkyl;
$R_2$ is hydroxymethyl or a lower, straight-chain or branched alkyl of at least 2 carbon atoms, which can be interrupted by one or more oxygen atoms, or is

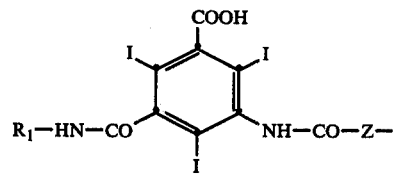

wherein Z is a carbon-to-carbon bond or a straight-chain or branched hydrocarbon which can be interrupted by one or more oxygen atoms, or when $R_1$ is other than —CH$_2$—CH$_2$—OH, is methyl; and the salts thereof with physiologically acceptable inorganic or organic bases, are x-ray contrast agents.

20 Claims, No Drawings

NOVEL IODIZED ISOPHTHALAMIC ACID COMPOUNDS

BACKGROUND OF THE INVENTION

The invention relates to novel x-ray contrast agents, the preparation thereof and to roentgenographic contrast media based thereon.

3-Acylamino-5-alkylcarbamoyl-2,4,6-triiodobenzoic acids are known from U.S. Pat. No. 3,145,197. Several amino acid derivatives of 3-acylamino-5-alkylcarbamoyl-2,4,6-triiodobenzoic acids have likewise been described, e.g., 5-acetamido-2,4,6-triiodoisophthaloyl diglycine in U.S. Pat. No. 3,102,880 and N-[3-N-(alkylacylamino)-5-alkylcarbamoyl-2,4,6-triiodobenzoyl]-amino acids in Helv. Chim. Acta 54 (8): 2551–2559 (1971). Although these compounds have a low toxicity, they have several undesirable side effects. For example, they do not meet the high requirements to be fulfilled by a medium for myelography, e.g., see Ugeskrift for laeger 134 (18): 936 (1972) and Advances in X-Ray Technology 115: 683–684 (1971).

Other teachings on highly iodinated aromatic compounds are those of Erich Klieger et al., U.S. Pat. No. 3,953,501; Heinz Gries et al., U.S. Pat. No. 4,001,298; Heinz Gries, U.S. Pat. No. 3,883,578; and Erich Klieger et al., Ser. No. 555,043, filed Mar. 3, 1975, now allowed, the disclosures of which are herein incorporated by reference.

SUMMARY OF THE INVENTION

In a compositional aspect, this invention relates to novel compounds of Formula I

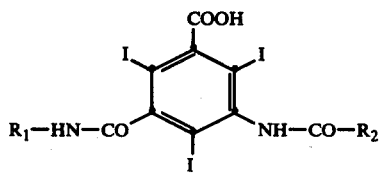

(I)

wherein $R_1$ is hydroxyalkyl of 2–6 carbon atoms; $R_2$ is hydroxymethyl, alkyl of up to 6 carbon atoms, oxaalkyl or dioxaalkyl whose alkyl is of up to 6 carbon atoms, wherein the oxygen atoms in the oxaalkylene or dioxaalkylene are separated from each other and from the ends thereof by at least one methylene, or

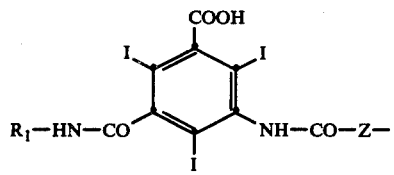

wherein Z is a carbon-to-carbon bond or a straight-chain or branched alkylene of up to 6 carbon atoms, or oxaalkylene, dioxaalkylene or trioxaalkylene of up to 6 carbon atoms in the alkylene, wherein the oxygen atoms in the oxaalkylene, dioxaalkylene or trioxaalkylene are separated from each other and from the ends thereof by at least one methylene, or when $R_1$ is other than —CH$_2$—CH$_2$—OH, is methyl; or a salt thereof with a physiologically acceptable base.

In another compositional aspect, this invention relates to an x-ray contrast agent adapted for parenteral administration, comprising in unit dosage form a radiopaque amount of a compound of Formula I, in admixture with a pharmaceutically acceptable carrier.

In a method of use aspect, this invention relates to a method for conducting a radiological examination of a patient which comprises administering thereto prior to examination a radiopaque amount of a compound of Formula I.

DETAILED DESCRIPTION $R_1$ is a branched-chain or straight-chain hydroxyalkyl of 2–6, preferably 2–5, carbon atoms. Straight-chain $R_1$ is preferably of 2–3 carbon atoms and branched-chain $R_1$ is preferably of 3–5 carbon atoms. Hydroxy in $R_1$ can be a primary or secondary hydroxy. Examples of $R_1$ include, but are not limited to 2-hydroxyethyl, 2-hydroxypropyl, 3-hydroxypropyl, 2-hydroxy-1,1-dimethylethyl and 3-hydroxy-1,1-dimethylpropyl.

Lower, straight-chain or branched alkyl $R_2$ can be of 1–6, preferably 2–5, carbon atoms, or can be a corresponding oxaalkyl, especially those of 1 or 2 oxygen atoms in $R_2$. Examples of $R_2$ are ethyl, propyl, isopropyl, butyl, isobutyl or tert.-butyl, methoxymethyl, methoxyethyl and $CH_3$—O—$(CH_2)_2$—O—$CH_2$.

In dimeric compounds of Formula I, Z is a carbon-to-carbon bond or a straight-chain or branched, preferably lower, hydrocarbyl residue which can be interrupted by one or more, preferably by one, two, or three, oxygen atoms. Preferred are straight-chain alkylene or oxaalkylene of 1–6, preferably 1–4, carbon atoms, of which examples are —$(CH_2)_4$— and —$(CH_2$—O—$CH_2)_2$—.

Compounds of Formula I, in the form of physiologically acceptable salts, include those with conventional inorganic and organic bases. The salts are prepared by reacting a corresponding acid with a base in a conventional manner.

Exemplary of suitable physiologically acceptable salts with bases are metallic salts, e.g., sodium, lithium, calcium, and magnesium salts; and amine salts, e.g., glucamine, N-methylglucamine, N,N-dimethylglucamine, ethanolamine, diethanolamine, and morpholine salts.

Salts of basic amino acids, for example, lysine, ornithine, arginine, and histidine salts, can also be used.

Compounds of Formula I therefore include those wherein:

(a) $R_1$ is hydroxyalkyl of 3–6 carbnon atoms;
(b) $R_1$ is hydroxyethyl;
(c) $R_2$ is hydroxymethyl, including each of (a)–(b);
(d) $R_2$ is alkyl of up to 6 carbon atoms, including each of (a)–(b);
(e) $R_2$ is oxaalkyl or dioxaalkyl of up to 6 carbon atoms in the alkyl, including each of (a)–(b);
(f) $R_2$ is

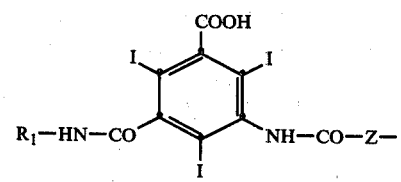

including each of (a)–(b);

(g) Z is a carbon-to-carbon bond, including each of (a)–(b);
(h) Z is alkylene of up to 6 carbon atoms, including each of (a)–(b);

(i) Z is oxaalkylene, dioxaalkylene or trioxaalkylene of up to 6 carbon atoms in the alkylene, including each of (a)–(b); and (j) $R_1$ is hydroxyalkyl of 3–6 carbon atoms and Z is methyl.

Compounds of Formula I are prepared by conventional acylation of a 5-amino-2,4,6-triiodophthalamic acid of Formula II

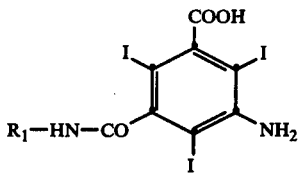

wherein $R_1$ is as above, with a reactive derivative of a monocarboxylic acid of the formula $R_2$—COOH wherein $R_2$ is as above, or with Hal—OC—Z—CO—Hal, wherein Hal is chlorine, bromine, or iodine and Z is as above; and, if desired, subsequently converting a thus-obtained free acid to a salt by reaction with an inorganic or organic base.

A corresponding acid halogenide (chloride, bromide, or iodide) or corresponding acid anhydride is preferred as a reactive derivative of a monocarboxylic acid $R_2$—COOH.

The acylation reaction is preferably carried out in a polar solvent at 0–150° C., more preferably 20–100° C., and most preferably at room temperature. Examples of solvents are acetonitrile, chlorobenzene, toluene, dioxane, tetrahydrofuran and dimethylformamide, but dimethylacetamide is preferred. However, an excess of the acylating agent can be used as solvent. If the acylation is done with an acid anhydride, it is advantageous to conduct the reaction in the presence of a catalytic amount of an acidic catalyst, preferably a mineral acid, such as sulfuric acid or perchloric acid, or of p-toluenesulfonic acid.

Conversion of an acid of Formula I to a salt thereof by reaction with an inorganic or organic base known to those skilled in the art is also done by conventional methods.

Compounds of Formula II are obtained, for example, from known 5-nitroisophthalic acid monomethyl ester, which is reacted with a corresponding substituted amine $R_1$-$NH_2$ to produce N-($R_1$)-5-nitroisophthalamic acid. Subsequently, nitro is reduced in a conventional manner to amino with hydrogen in the presence of catalytic Raney nickel. The three iodine atoms are introduced by a conventional manner using $KICl_2$ or ClI.

Compounds of Formula I are highly suitable radiopaque substances for the preparation of and/or for utilization in x-ray contrast media. The compounds have the properties required of x-ray contrast agents, that is:

(1) they are very soluble in water;
(2) aqueous solutions, even if highly concentrated, have the necessary stability;
(3) the compounds are readily excretable via the urine; and
(4) the novel compounds of Formula I have low toxicity.

In the following table, compounds 2–7 are compared to the conventional ioxithalamic acid (1), in tests on rats conducted by customary methods with aqueous meglumine salt solutions of the corresponding test compounds:

TABLE

| Compound | $R_1$ | $R_2$ | $LD_{50}$ (i.v.) g. Acid/kg. | Valzelli Value ($ED_{50}$:mg. I/kg. and Confidence Range p 0.05) |
|---|---|---|---|---|
| 1 | —$CH_2CH_2OH$ | —$CH_3$ | 15.2 | 12.3 (10.3–14.4) |
| 2 | —C(CH$_3$)(CH$_3$)—$CH_2OH$ | —$CH_2$—O—$CH_3$ | 20.0 | 71.4 (61.4–99.9) |
| 3 | —$CH_2CH(OH)$—$CH_3$ | —$CH_2$—O—$CH_3$ | 19.0 | 44.6 (35.5–52.2) |
| 4 | —$CH_2$—$CH_2$—$CH_2$—OH | —$CH_2O$—$CH_3$ | 16.3 | 43.1 (32.6–50.9) |
| 5 | —$CH_2$—$CH_2OH$ | —$CH_2$—$OCH_3$ | >18.6 | 44.9 (36.7–51,8) |
| 6 | —C(CH$_3$)(CH$_3$)—$CH_2$—$CH_2OH$ | —$CH_2$—O—$CH_3$ | 18,4 | 67.2 (58.7–84.8) |
| 7 | —$CH_3$—CH(OH)—$CH_3$ | —$CH_3$ | 18.2 | 50.7 (44.3–56.6) |

The table shows that the compounds of Formula I are clearly superior to conventional ioxithalamic acid (1) both with respect to general compatibility ($LD_{50}$), i.e., low toxicity, and especially with respect to neural compatibility, evaluated as intracerebral compatibility or Valzelli value, in accordance with Valzelli, Med.Exp. 11 : 23–26 (1964).

Compounds of Formula I are radiopaque and can be used in medical practice as x-ray contrast media, in the form of free acids, the salts, or mixtures of the salts. Because of very high water solubility and excretability via the urine, they are particularly suitable for use in urography, angiography and myelography.

Novel x-ray contrast media based on compounds of Formula I are prepared by bringing the radiopaque compound, optionally as a salt with a physiologically compatible base, and additives customary in galenic pharmacy into a form suitable for intravenous administration. Customary additives include, but are not limited to, disodium edetate and calcium edetate.

The compounds of this invention can be employed in mixture with conventional excipients, i.e., pharmaceutically acceptable organic or inorganic carrier substances suitable for parenteral or enteral application which do not deleteriously react with the active compounds. Suitable pharmaceutically acceptable carriers include but are not limited to water, salt solutions, alcohols, vegetable oils, polyethylene glycols, viscous paraffin, perfume oil, fatty acid monoglycerides and diglycerides, pentaerythritol fatty acid esters, hydroxy-methylcellulose, polyvinyl pyrrolidone, talc, etc.

For parenteral application, solutions, preferably oily or aqueous solutions, as well as suspensions or emulsions, are particularly suitable. Ampoules are convenient unit dosages.

For intravenous administration the compounds of this invention are preferably used in aqueous solution whereby the concentration of the active compound is preferably between about 15% by volume and about 75% by volume. Generally the amount of active agent per unit dosage is about 5 to 50 g., preferably 7 to 35 g.

The solutions are characterized by a relatively low viscosity and can be administered by intravenous injection. The solutions are furthermore distinguished by good circulatory compatibility and low toxicity.

Owing to the high solubility in water of compounds of Formula I, solutions containing about 5–45% of bound iodine, i.e., salt solutions containing approximately 10-100 g. of radiopaque compound of Formula I per 100 ml. of solution, can be prepared for intravenous administration.

The following examples serve to further explain the present invention.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever. In the following Examples, the temperatures are set forth uncorrected in degrees Celsius; unless otherwise indicated, all parts and percentages are by weight.

EXAMPLE 1

N-(2-Hydroxy-1,1-dimethylethyl)-2,4,6-triiodo5-methoxyamidoisophthalamic Acid (a) A solution of 112.6 g. (0.5 mol) of the monomethyl ester of 5-nitroisophthalic acid in 500 ml. of methanol is combined with 191.7 ml. of 2-amino-2-methyl-1-propanol and the solution stirred and heated under reflux for 12 hours. At this point, the reaction is finished as determined by a thin-layer chromatogram: thin-layer systems: toluene/glacial acetic acid/ethyl acetate/methanol (360/240/240/180) and dioxane/water/concentrated ammonia (700/175/35). Thereafter, the reaction mixture is concentrated under vacuum, the residue is treated in 2,500 ml. of water with active carbon, the carbon is removed, and the reaction mixture is acidified with concentrated hydrochloric acid with stirring and then further stirred for several hours. Subsequently, the mixture is vacuum-filtered from the precipitate, carefully washed free of salt with water, and the product is dried under vacuum at 70° C., thus obtaining 135 g. (96% of theory) of N-(2-hydroxy-1,1-dimethylethyl)-5-nitroisophthalamic acid, m.p. 209°–210° C.

(b) With the addition of 175 ml. of 2N ammonia, 98.7 g. (350 millimoles) of N-(2-hydroxy-1,1-dimethyl)-5-nitroisophthalamic acid is dissolved in 800 ml. of water and then hydrogenated at room temperature with 10% Raney nickel as the catalyst at about 120 atmospheres gauge. After the catalyst has been removed, the hydrogenation solution is brought to 39.2 liters with water. With agitation, 700 ml. of concentrated hydrochloric acid and 700 ml. of 2N KICl$_2$ solution are added to the reaction mixture, which is stirred for 3 days at room temperature. Thereafter, the mixture is vacuum-filtered from the precipitate, carefully washed with water, and dried under vacuum at 70° C., thus obtaining 169.8 g. (77% of theory) of 5-amino-N-(2-hydroxy-1,1-dimethylethyl)-2,4,6-triiodoisophthalamic acid; m.p. 275°–276° C., with decomposition.

(c) At a maximum of 10° C., 26.1 ml. (360 mmol) of thionyl chloride is added dropwise with stirring within 30 minutes to 27.3 ml. (360 mmol) of methoxyacetic acid in 90 ml. of dimethylacetamide. After the mixture has been agitated for another hour at 0° C., the solution is combined dropwise at a maximum of 8° C. with stirring with 56.7 g. (90 mmol) of 5-amino-N-(2-hydroxy-1,1-dimethylethyl)-2,4,6-triiodoisophthalamic acid, m.p. 275°–276° C. (decomposition) in 90 ml. of dimethylacetamide during the course of 45 minutes. The mixture is then stirred for another hour at 0° C. and thereafter overnight at room temperature. Then, 20 ml. of water is added thereto and the mixture is concentrated under vacuum after stirring for 30 minutes. The residue is then heated for 1 hour to about 80° C. in 540 ml. of water, agitated overnight at room temperature, and the precipitate is vacuum-filtered and washed with water. The product is then treated in 90 ml. of 2N sodium hydroxide solution with 5 g. of active carbon for 1 hour, whereafter the carbon is removed, the filtrate is acidified with concentrated hydrochloric acid, stirred for 16 hours at room temperature, vacuum-filtered, washed free of salt with water, and dried under vacuum at 70° C., thus producing 56.3 g. (89% of theory) of N-(2-hydroxy-1,1-dimethylethyl)-2,4,6-triiodo-5-methoxyacetamidoisophthalamic acid, m.p. 285°–286° C.

EXAMPLE 2

N-(2-Hydroxypropyl)-2,4,6-triiodo-5-methoxyacetamidoisophthalamic Acid (a) 225.2 g. (1.0 mol) of the monomethyl ester of 5-nitroisophthalic acid in 1,000 ml. of methanol and 310 ml. of 1-amino-2-propanol is reacted with heating for 14 hours under reflux analogously to Example 1(a) and then worked up, yielding 221.0 g. (82%) of N-(2-hydroxypropyl)-5-nitroisophthalamic acid, m.p. 195°–196° C.

(b) 214.5 g. (800 mmol) of the aforementioned N-(2-hydroxypropyl)-5-nitroisophthalamic acid, m.p. 195°–196° C., is dissolved in 200 ml. of water while adding 400 ml. of 2N ammonia, and then hydrogenated at about 100 atmospheres gauge with 10% Raney nickel as the catalyst. The reaction mixture is thereafter filtered off from the catalyst and, after adding 1.6 l. of concentrated hydrochloric acid and 1.6 l. of 2N KICl$_2$ solution, agitated for 3 days at room temperature. The mixture is filtered off from the precipitate, which is carefully washed free of salt and dried under vacuum at 20° C. Yield: 389.3 g. (79%) of 5-amino-N-(2-hydroxypropyl)-2,4,6-triiodophthalamic acid, m.p. 247°–248° C., with decomposition.

(c) Analogously to Example 1(c), 61.59 g. (100 mmol) of 5-amino-N-(2-hydroxypropyl)-2,4,6-triiodoisophthalamic acid is reacted with methoxyacetyl chloride, freshly prepared from 30.3 ml. of methoxyacetic acid and 29 ml. of thionyl chloride in dimethylacetamide. Yield: 53.8 g. (78%) of N-(2-hydroxypropyl)-2,4,6-triiodo-5-methoxyacetamidoisophthalamic acid, m.p. 263°–265° C., with decomposition.

EXAMPLE 3

N-(2-Hydroxypropyl)-2,4,6-triiodo-5-(2-methoxyethoxyacetamido)-isophthalamic Acid At a maximum of 10° C. (ice cooling), 16.5 ml. of methoxyethoxyacetyl chloride is added dropwise within 30 minutes with agitation to 30.8 g. (50 mmol) of 5-amino-(2-hydroxypropyl)2,4,6-triiodoisophthalamic acid in 60 ml. of dimethylacetamide. The mixture is stirred for 1 hour at 0° C. and then for 16 hours at room temperature. Thereafter, another 2 ml. of the acid chloride is added thereto, and the mixture is stirred at room temperature for 4 hours. Then, 10 ml. of water is added and the mixture is concentrated under vacuum. The residue is dissolved in 350 ml. of water and neutralized with 32% sodium hydroxide solution. The mixture is combined with another 5 ml. of 32% sodium hydroxide solution and then stirred for some time after adding 5 g. of active carbon. After the carbon has been removed, the mixture is acidified with concentrated hydrochloric acid, allowed to stand for a period of time and vacuum-filtered. The resulting precipitate is dried under vacuum. Yield: 21.3 g. (58%), m.p. 275° C., with decomposition.

EXAMPLE 4

5-Hydroxyacetamido-N-(2-hydroxypropyl)-2,4,6-triiodoisophthalamic Acid

At temperatures no higher than 10° C., 13.3 ml. of acetoxyacetyl chloride is gradually added dropwise with agitation to a solution of 30.8 g. (50 mmol) of 5-amino-(2-hydroxypropyl)-2,4,6-triiodoisophthalamic acid in 60 ml. of dimethylacetamide. After 16 hours of agitation at room temperature and the addition of 10 ml. of water, the mixture is stirred for 30 minutes at room temperature and then concentrated under vacuum. The residue, after having been treated repeatedly with fresh water, is saponified on a steam bath with agitation with 70 ml. of 2N sodium hydroxide solution in 250 ml. of water. After cooling, the reaction mixture is acidified with 12.5 ml. of concentrated hydrochloric acid, stirred for 16 hours at room temperature, and, after adding approximately the same volume of saturated NaCl solution, allowed to stand for 4 days. Thereafter, the mixture is vacuum-filtered from the thus-separated precipitate, which is washed with minimum portions of water and dried under vacuum. Yield: 17.2 g. (51%), m.p. 275°–277° C., with decomposition.

EXAMPLE 5

N-(3-Hydroxypropyl)-2,4,6-triiodo-5-methoxyacetamidoisophthalamic Acid (a) Analogously to Example 1(a), 112.6 g. (500 mmol) of the monomethyl ester of 5-nitroisophthalic acid in 500 ml. of methanol is refluxed with 147 ml. of 3-amino-1-propanol for 16 hours and then worked up, thus producing 119.3 g. (89%) of N-(3-hydroxypropyl)-5-nitroisophthalamic acid, m.p. 163°–164° C.

(b) 93.7 g. (350 mmol) of N-(3-hydroxypropyl)-5-nitroisophthalamic acid, dissolved in 720 ml. of water and 180 ml. of 2N ammonia are hydrogenated at about 100 atmospheres gauge with the addition of 10% Raney nickel. The catalyst is removed, and the solution is brought to 1,750 ml. with water and added dropwise with agitation within 2 hours to a solution, heated to 75–80° C., of 4,550 ml. of water, 630 ml. of concentrated hydrochloric acid and 105 ml. of 94% ClI. The mixture is stirred for 4 hours at this temperature and then for 16 hours at room temperature. The mixture is vacuum-filtered from the thus-obtained precipitate, and the latter is washed free of salt with water and dried under vacuum at 70° C. For further purification, reprecipitation is optionally effected by way of the ammonium salt using of active carbon, thus producing 167.9 g. (78%) of 5-amino-N-(3-hydroxypropyl)-2,4,6-triiodoisophthalamic acid; m.p. 211°–213° C., with decomposition.

(c) 76.8 g. (125 mmol) of 5-amino-N-(3-hydroxypropyl)2,4,6-triiodoisophthalamic acid and 37.9 ml. of methoxyacetic acid/36.3 ml. of thionyl chloride in dimethylacetamide are reacted analogously to Example 1(c), thus obtaining 53.3 g. (62%) of N-(3-hydroxypropyl)-2,4,6-triiodo-5-methoxyacetamidoisophthalamic acid, m.p. 210° C. (sintering) up to approximately 265° C. (decomposition).

EXAMPLE 6

N-(2-Hydroxyethyl)-2,4,6-triiodo-5-methoxyacetamidoisophthalamic Acid

Analogously to Example 1(c), 90.3 g. (150 mmol) of 5-amino-N-(2-hydroxyethyl)-2,4,6-triiodoisophthalamic acid and methoxyacetyl chloride, freshly prepared from 45.5 ml. of methoxyacetic acid/43.5 ml. of thionyl chloride, are reacted in dimethylacetamide; yield: 84.7 g. (84%) m.p. 285° C., with decomposition.

EXAMPLE 7

N-(3-Hydroxy-1,1-dimethylpropyl)-2,4,6-triiodo5-methoxyacetamidoisophthalamic Acid (a) Analogously to Example 1(a), using 112.6 g. (500 mmol) of nitroisophthalic acid monomethyl ester and 244.3 ml. of 3-amino-3-methyl-1-butanol in 1,000 ml. of methanol, 114 g. (77%) of N-(3-hydroxy-1,1-dimethylpropyl)-5-nitroisophthalamic acid, m.p. 181°–182° C., is prepared by 40 hours of heating under reflux.

(b) 88.9 g. (300 mmol) of N-(3-hydroxy-1,1-dimethylpropyl)-5-nitroisophthalamic acid is hydrogenated in 750 ml. of water and 150 ml. of 2N ammonia at about 85 atmospheres gauge in the presence of 10% Raney nickel. The catalyst is separated and the hydrogenation solution is brought with water to 33.6 l. After the addition of, respectively, 600 ml. of concentrated hydrochloric acid and 2N $KICl_2$, the mixture is stirred for 3 days at room temperature. The thus-formed solid is vacuum-filtered, carefully washed free of salt with water, and dried under vacuum at 70° C., thus producing 150.2 g. (78%) of 5-amino-N-(3-hydroxy-1,1-dimethylpropyl)-2,4,6-triiodoisophthalamic acid, m.p. 253°–255° C., with decomposition.

(c) 64.4 g. (100 mmol) of 5-amino-N-(3-hydroxy-1,1-dimethylpropyl)-2,4,6-triiodoisophthalamic acid and methoxyacetyl chloride, prepared from 30.3 ml. of methoxyacetic acid and 29 ml. of thionyl chloride, in dimethylacetamide are reacted analogously to Example 1(c), thus producing a yield of 61.0 g. (85%) of N-(3-hydroxy-1,1-dimethylpropyl)-2,4,6-triiodo-5-methoxyacetamidoisophthalamic acid, m.p. 287°–288° C., with decomposition.

EXAMPLE 8

N-(2-Hydroxypropyl)-2,4,6-triiodo-5-propionylamidoisophthalamic Acid

As in Example 3, 5-amino-N-(2-hydroxypropyl)2,4,6-triiodoisophthalamic acid is reacted with propionyl chloride in dimethylacetamide; yield: 73%, m.p. 267°–269° C., with decomposition.

EXAMPLE 9

N-(2-Hydroxypropyl)-2,4,6-triiodo-5-valerylamidoisophthalamic Acid

5-Amino-N-(2-hydroxypropyl)-2,4,6-triiodoisophthalamic acid and valeryl chloride in dimethylacetamide are reacted analogously to Example 3. Yield: 75%, m.p. 264°–266° C., with decomposition.

EXAMPLE 10

5,5'-(3,6-Dioxaoctanedioyldiimino)-bis[N-(2-hydroxy-1,1-dimethylethyl)-2,4,6-triiodoisophthalamic Acid]

18.9 g. (30 mmol) of 5-amino-N-(2-hydroxy-1,1-dimethylethyl)-2,4,6-triiodoisophthalamic acid, dissolved in 36 ml. of dimethylacetamide, is combined at 0° C. under agitation dropwise with 2.91 ml. of dioxaoctanoic acid dichloride. The mixture is agitated for 1 hour at 0° C. and then overnight at room temperature. Thereafter, another 1.25 ml. of dioic acid dichloride is added thereto and the mixture stirred for 3 days at room temperature. The reaction mixture is then poured into 400 ml. of water and, after 4 hours of agitation, the thus-formed precipitate is vacuum-filtered. The precipitate is then dissolved in a solution of 22.5 g. of soda in 225 ml. of water and agitated for 3 days. The solution is treated with active carbon, and acidified with concentrated hydrochloric acid after the carbon has been removed. After 16 hours of agitation, the thus-precipitated product is vacuum-filtered, washed free of salt with water, and dried under vacuum at 70° C. Yield: 15.0 g. (71%), m.p. 285°–286° C., with decomposition.

EXAMPLE 11

5,5'-Hexanedioyldiimino-bis[N-(2-hydroxy-1,1-dimethylethyl)-2,4,6-triiodoisophthalamic Acid]

Analogously to Example 10, 5-amino-N-(2-hydroxy-1,1-dimethylethyl)-2,4,6-triiodoisophthalamic acid is reacted with hexanedioic acid dichloride in dimethylacetamide, and the reaction mixture is worked up. The thus-obtained product melts at 280°–281° C., with decomposition.

EXAMPLE 12

5,5'-Hexanedioyldiimino-bis[N-(2-hydroxypropyl)2,4,6-triiodoisophthalamic Acid]

Analogously to Example 10, 5-amino-N-(2-hydroxypropyl)2,4,6-triiodoisophthalamic acid is reacted with hexanedioic acid dichloride in dimethylacetamide and then worked up. The thus-obtained product melts at 284°–285° C., with decomposition.

EXAMPLE 13

Production of a Ready-for-Use Methylglucamine Salt Solution:

| | |
|---|---|
| N-(2-Hydroxy-1,1-dimethylethyl)-2,4,6-triiodo-5-methoxyacetamidoisophthalamic acid | 700.70 g. |
| N-Methylglucamine | 194.85 g. |
| Disodium edetate | 0.10 g. |
| Twice distilled water | to 1,000.00 ml. |

The solution is charged into ampoules or multivials and sterilized at 120° C. The solution contains 380 mg. I/ml.

EXAMPLE 14

Production of a Ready-for-Use Sodium Salt Solution:

| | |
|---|---|
| N-(2-Hydroxy-1,1-dimethylethyl)-2,4,6-triiodo-5-methoxyacetamidoisophthalamic acid | 553.18 g. |
| Sodium hydroxide | 31.52 g. |
| Disodium edetate | 0.10 g. |
| Twice distilled water | to 1,000.00 ml. |

The solution is charged into ampoules or multivials and sterilized at 120° C. The solution contains 300 mg. I/ml.

EXAMPLE 15

| | |
|---|---|
| N-(2-Hydroxyethyl)-2,4,6-triiodo-5-methoxyacetamidoisophthalamic acid | 672.70 g. |
| N-Methylglucamine | 194.85 g. |
| Didodium edetate | 0.10 g. |
| Twice distilled water | to 1,000.00 ml. |

The solution is charged into ampoules or multivials and sterilized at 120° C. The solution contains 380 mg. I/ml.

EXAMPLE 16

| | |
|---|---|
| N-(2-Hydroxypropyl)-2,4,6-triiodo-5-methoxyacetamidoisophthalmic acid | 542.13 g. |
| Sodium hydroxide | 31.52 g. |
| Disodium edetate | 0.10 g. |
| Twice distilled water | to 1,000.00 ml. |

The solution is charged into ampoules or multivials and sterilized at 120° C. The solution contains 300 mg. I/ml.

EXAMPLE 17

5-Acetamido-N-(2-hydroxy-1,1-dimethylethyl)2,4,6-triiodoisophthalamic Acid

Analogously to Example 3, 63.0 g. (100 mmol) of 5-amino-N-(2-hydroxy-1,1-dimethylethyl)-2,4,6-triiodoisophthalamic acid is reacted in 120 ml. of dimethylacetamide with 17 ml. of acetyl chloride and worked up. Yield: 64.0 g. (95%), m.p. 279°–281° C., with decomposition.

EXAMPLE 18

5-Acetamido-N-(3-hydroxypropyl)-2,4,6-triiodoisophthalamic Acid

5-Amino-N-(2-hydroxypropyl-2,4,6-triiodoisophthalamic acid and acetyl chloride in dimethylacetamide are reacted analogously to Example 3. Yield: 45%, m.p. 277°–279° C., with decomposition.

EXAMPLE 19

5-Acetamido-N-(2-hydroxypropyl)-2,4,6-triiodoisophthalamic Acid

Analogously to Example 3, 5-amino-N-(2-hydroxypropyl)2,4,6-triiodoisophthalamic acid and acetyl chloride are reacted in dimethylacetamide. Yield: 87%, m.p. 276°–278° C., with decomposition.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound of the formula

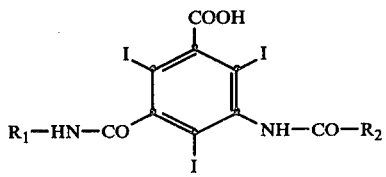

wherein $R_1$ is hydroxyalkyl of 2–6 carbon atoms;

$R_2$ is (a) hydroxymethyl, (b) alkyl of 2–6 carbon atoms, (c) oxaalkyl or dioxaalkyl whose alkyl is of up to 6 carbon atoms, wherein the oxygen atoms in the oxaalkylene or dioxaalkylene are separated from each other and from the ends thereof by at least one methylene, or (d) when $R_1$ is other than $-CH_2-CH_2-OH$, is methyl; or a salt thereof with a physiologically acceptable base.

2. N-(2-Hydroxy-1,1-dimethylethyl)-2,4,6-triiodo-5-methoxyacetamidoisophthalamic acid, a compound of claim 1.

3. N-(2-Hydroxypropyl)-2,4,6-triiodo-5-methoxyacetamidoisophthalamic acid, a compound of claim 1.

4. N-(2-Hydroxypropyl)-2,4,6-triiodo-5-(2-methoxyethoxyacetamido)-isophthalamic acid, a compound of claim 1.

5. 5-Hydroxyacetamido-N-(2-hydroxypropyl)-2,4,6-triiodoisophthalamic acid, a compound of claim 1.

6. N-(3-Hydroxypropyl)-2,4,6-triiodo-5-methoxyacetamidoisophthalamic acid, a compound of claim 1.

7. N-(2-Hydroxyethyl)-2,4,6-triiodo-5-methoxyacetamidoisophthalamic acid, a compound of claim 1.

8. N-(3-Hydroxy-1,1-dimethylpropyl)-2,4,6-triiodo-5-methoxyacetamidoisophthalamic acid, a compound of claim 1.

9. N-(2-Hydroxypropyl)-2,4,6-triiodo-5-propionylamidoisophthalamic acid, a compound of claim 1.

10. N-(2-Hydroxypropyl)-2,4,6-triiodo-5-valerylamidoisophthalamic acid, a compound of claim 1.

11. 5,5'-(3,6-Dioxaoctanedioyldiimino)-bis[N-(2-hydroxy-1,1-dimethylethyl)-2,4,6-triiodoisophthalamic acid], a compound of claim 1.

12. 5,5'-Hexanedioyldiimino-bis[N-(2-hydroxy-1,1-dimethylethyl)-2,4,6-triiodoisophthalamic acid], a compound of claim 1.

13. 5,5'-Hexanedioyldiimino-bis[N-(2-hydroxypropyl)-2,4,6-triiodoisophthalamic acid], a compound of claim 1.

14. 5-Acetamido-N-(2-hydroxy-1,1-dimethylethyl)-2,4,6-triiodoisophthalamic acid, a compound of claim 1.

15. 5-Acetamido-N-(3-hydroxypropyl)-2,4,6-triiodoisophthalamic acid, a compound of claim 1.

16. 5-Acetamido-N-(2-hydroxypropyl)-2,4,6-triiodoisophthalamic acid, a compound of claim 1.

17. An x-ray contrast agent adapted for parenteral administration, comprising in unit dosage form a radiopaque amount of a compound of claim 1, in admixture with a pharmaceutically acceptable carrier.

18. A method for conducting a radiological examination of a patient which comprises administering thereto prior to examination a radiopaque amount of a compound of claim 1.

19. The X-ray contrast agent of claim 17, wherein the amount of radiopaque compound is 15–75 volume %.

20. The X-ray contrast agent of claim 17, wherein the amount of radiopaque compound per unit dosage is 5–50 grams.

* * * * *